US006953082B2

US006953082B2

(12) United States Patent
Costello et al.

(10) Patent No.: US 6,953,082 B2
(45) Date of Patent: Oct. 11, 2005

(54) HYDROFLUOROETHER AS A HEAT-TRANSFER FLUID

(75) Inventors: Michael G. Costello, Afton, MN (US); Richard M. Flynn, Mahtomedi, MN (US); Frederick E. Behr, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 65 days.

(21) Appl. No.: 10/738,372

(22) Filed: Dec. 16, 2003

(65) Prior Publication Data

US 2005/0126756 A1   Jun. 16, 2005

(51) Int. Cl.[7] .............................. F28C 3/00; C09K 5/10
(52) U.S. Cl. ............... 165/80.4; 165/80.5; 165/104.33; 252/78.1
(58) Field of Search .............................. 252/67–70, 73, 252/77, 78.1, 570; 165/80.4, 80.5, 104.19, 165/104.28, 104.31, 104.33, 104.11; 568/683; 118/724, 725

(56) References Cited

U.S. PATENT DOCUMENTS

| | | | |
|---|---|---|---|
| 3,362,180 A | * | 1/1968 | Eiseman, Jr. ................. 62/112 |
| 3,549,711 A | | 12/1970 | Merrill et al. |
| 3,739,033 A | | 6/1973 | Anello et al. |
| 3,962,348 A | | 6/1976 | Benninger et al. |
| 4,079,084 A | | 3/1978 | Houghton |
| 5,713,211 A | | 2/1998 | Sherwood |
| 5,750,797 A | | 5/1998 | Vitcak et al. |
| 5,847,048 A | | 12/1998 | Feiring |
| 5,925,611 A | | 7/1999 | Flynn et al. |
| 6,205,799 B1 | * | 3/2001 | Patel et al. ................... 62/132 |
| 6,297,308 B1 | * | 10/2001 | Jariwala et al. ............. 524/462 |
| 6,303,080 B1 | * | 10/2001 | Tuma .......................... 422/38 |
| 6,347,907 B1 | | 4/2002 | Touslgnant et al. |
| 6,374,907 B1 | * | 4/2002 | Tousignant et al. ........ 165/80.4 |
| 6,429,400 B1 | * | 8/2002 | Sawada et al. ........ 219/121.52 |
| 6,746,620 B2 | * | 6/2004 | Maccone et al. ............. 252/70 |
| 6,866,094 B2 | * | 3/2005 | Cousineau et al. ......... 165/278 |

FOREIGN PATENT DOCUMENTS

| | | |
|---|---|---|
| FR | 2 287 432 | 5/1976 |
| GB | 1 354 138 | 5/1974 |
| JP | 62-103034 | 5/1987 |
| SU | 1810324 A1 | 4/1993 |
| WO | WO 02/102858 | 12/2002 |

OTHER PUBLICATIONS

G. Sherwood, "Secondary Heat Transfer Systems and the Application of a New Hydrofluoroether", Oct. 1995, Presented at the International CFC & Halon Alternatives Conference in Washington, D.C., 11 pages.*

Aldrich et al., "α-Fluorinated Ethers. II. Alkyl Fluoroalkyl Ethers," *J. Org. Chem.*, 29(1) 11-15 (1964).

Blazejewski et al., "Synthesis of 2-trifluoromethoxyethyl trifluoromethoxyacetate and derived 2-trifluoromethoxyacrylates," *J. Fluorine Chem.*, 117(2) 161-166 (2002).

Chi et al., "A Facile Synthesis of Partly-fluorinated Ethers Using Perfluoropropoxyethylene and Aliphatic Alcohols," *Bull, Korean Chem Soc.*, 20(2) 220-222 (1999).

Sievert et al., "Synthesis of Perfluorinated Ethers by an Improved Solution Phase Direct Fluorination Process," *J. Fluorine Chem.*, 53, 397-417 (1991).

\* cited by examiner

*Primary Examiner*—Evan Pert
(74) *Attorney, Agent, or Firm*—Colene H. Blank

(57) ABSTRACT

The present invention comprises a compound represented by the following structure:

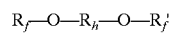

wherein:
  O is oxygen;
  $R_f$ and $R_f'$ are, independently, a perfluoroaliphatic group; and
  $R_h$ is independently a linear, branched or cyclic alkylene group having from 2 to about 8 carbon atoms and at least 4 hydrogen atoms, and
  wherein the hydrofluoroether compound is free of —O—$CH_2$—O—.

Another embodiment is an apparatus comprising a device and a mechanism for heat transfer comprising a hydrofluoroether heat-transfer fluid.

Another embodiment of the present invention is a method for heat transfer.

18 Claims, No Drawings

HYDROFLUOROETHER AS A HEAT-TRANSFER FLUID

FIELD OF INVENTION

This invention relates to hydrofluoroether heat-transfer fluids.

BACKGROUND

Presently various fluids are used for heat transfer. The suitability of the heat-transfer fluid depends upon the application process. For example, some electronic applications require a heat-transfer fluid which is inert, has a high dielectric strength, has low toxicity, good environmental properties, and good heat transfer properties over a wide temperature range. Other applications require precise temperature control and thus the heat-transfer fluid is required to be a single phase over the entire process temperature range and the heat-transfer fluid properties are required to be predictable, i.e., the composition remains relatively constant so that the viscosity, boiling point, etc. can be predicted so that a precise temperature can be maintained and so that the equipment can be appropriately designed.

In the semiconductor industry, there are numerous devices or processes that require a heat-transfer fluid having select properties. The heat-transfer fluid may be used to remove heat, add heat, or maintain a temperature.

Each of the semiconductor processes described below incorporates a device or a work-piece which has heat removed from it or has heat added to it. The heat transfer associated with either the heat removal or addition can take place over a wide temperature range. Thus, in each case a heat-transfer fluid is preferably used which has other attributes that make it "operator friendly". In order for a heat-transfer fluid to be considered "operator friendly", the heat-transfer fluid preferably exhibits low toxicity and low flammability.

For automated test equipment (ATE), equipment is used to test the performance of semiconductor dice. The dice are the individual "chips" that are cut from a wafer of semiconductor substrate. The dice come from the semiconductor foundry and must be checked to ensure they meet functionality requirements and processor speed requirements. The test is used to sort "known good dice" (KGD) from dice that do not meet the performance requirements. This testing is generally performed at temperatures ranging from about −80° C. to about 100° C.

In some cases the dice are tested one-by-one, and an individual die is held in a chuck. This chuck provides, as part of its design, provision for cooling the die. In other cases, several dice are held in the chuck and are tested either sequentially or in parallel. In this situation, the chuck provides cooling for several dice during the test procedure.

It may also be advantageous to test dice at elevated temperatures to determine their performance characteristics under conditions of elevated temperature. In this case, a coolant which has good heat-transfer properties well above room temperature is advantageous.

In some cases, the dice are tested at very low temperatures. For example, Complementary Metal-Oxide Semiconductor ("CMOS") devices in particular operate more quickly at lower temperatures.

If a piece of ATE equipment employs CMOS devices "on board" as part of its permanent logic hardware, it may be advantageous to maintain the logic hardware at a low temperature.

Therefore, to provide maximum versatility to the ATE, a heat-transfer fluid preferably performs well at both low and high temperatures (i.e., preferably has good heat transfer properties over a wide temperature range), is inert (i.e., is non-flammable, low in toxicity, non-chemically reactive), has high dielectric strength, has a low environmental impact, and has predictable heat-transfer properties over the entire operating temperature range.

Etchers operate over temperatures ranging from about 70° C. to about 150° C. In this process, reactive plasma is used to anisotropically etch the features in a wafer. The wafers to be processed are kept at a constant temperature at each selected temperature. Therefore, the heat-transfer fluid preferably is a single phase over the entire temperature range. Additionally, the heat-transfer fluid preferably has predictable performance over the entire range so that the temperature can be precisely maintained.

Ashers operate over temperatures ranging from about 40° C. to about 150° C. This is a process that removes the photosensitive organic "mask".

Steppers operate over temperatures ranging from about 40° C. to about 80° C. This is the process step in semiconductor manufacturing where the reticules needed for manufacturing are produced. Reticules are used to produce the patterns of light and shadow needed to expose the photosensitive mask. The film used in the steppers is typically maintained within a temperature window of +/−0.2° C. to maintain good performance of the finished reticule.

PECVD (plasma enhanced chemical vapor deposition) chambers operate over temperatures ranging from about 50° C. to about 150° C. In this process, films of silicon oxide, silicon nitride, and silicon carbide are grown on a wafer by the chemical reaction initiated in a reagent gas mixture containing silicon and either: 1) oxygen; 2) nitrogen; or 3) carbon. The chuck on which the wafer rests is kept at a uniform, constant temperature at each selected temperature.

Heat-transfer fluids which are presently used in these semiconductor applications include perfluorocarbons (PFCs), perfluoropolyethers (PFPEs), perfluoroamines (PFAs), perfluoroethers (PFEs), water/glycol mixtures, deionized water, silicone oils and hydrocarbon oils. However, each of these heat-transfer fluids has some disadvantage. PFCs, PFPEs, PFAs and PFEs may exhibit atmospheric lifetime values of greater than 500 years, and up to 5,000 years. Additionally, these materials may exhibit high global warming potentials ("GWP"). GWP is the integrated potential warming due to the release of one (1) kilogram of sample compound relative to the warming due to one (1) kilogram of $CO_2$ over a specified integration time horizon. Water/glycol mixtures are temperature limited, that is, a typical low temperature limit of such mixtures is −40° C. At low temperatures water/glycol mixtures also exhibit relatively high viscosity. The high viscosity at low temperature yields high pumping power. Deionized water has a low temperature limit of 0° C. Silicone oils and hydrocarbon oils are typically flammable.

Removing heat from electronic devices has become one of the most important obstacles to further improving processor performance. As these devices become more powerful, the amount of heat generated per unit time increases. Therefore, the mechanism of heat transfer plays an important role in processor performance. The heat-transfer fluid preferably has good heat transfer performance, good electrical compatibility (even if used in "indirect contact" applications such as those employing cold plates), as well as low toxicity, low (or non-) flammability and low environmental impact. Good electrical compatibility requires the heat-transfer fluid candidate to exhibit high dielectric strength, high volume resistivity, and poor solvency for polar materials. Additionally, the heat-transfer fluid candidate must exhibit good mechanical compatibility, that is, it must not affect typical materials of construction in an adverse manner. In this application, heat-transfer fluid candidates are disqualified if their physical properties are not stable over time.

Materials currently used as heat-transfer fluids for cooling electronics or electrical equipment include PFCs, PFPEs, silicone oils, and hydrocarbon oils. Each of these heat-transfer fluids has some disadvantage. PFCs and PFPEs may be environmentally persistent. Silicone oils and hydrocarbon oils are typically flammable.

Thermal shock testing is generally performed at temperatures ranging from about −65° C. to about 150° C. The rapid cycling of temperature in a part or device may be required to simulate the thermal changes brought on by, for instance, launching a missile. Thermal shock testing is required for electronics used for military missiles, among other things. There are several military specifications related to thermal shock testing of many electronic components and assemblies. This test uses various means of imparting rapidly changing temperatures within a part or electronic device. One such device employs a liquid heat-transfer fluid or liquid heat-transfer fluids that are kept in separate reservoirs maintained at temperature extremes where parts are alternately immersed to induce thermal shock to the test part. Typically, operators load and unload the components or assemblies to and from the thermal shock equipment. Therefore, it is important that a heat-transfer fluid used in such an application exhibit low toxicity, low flammability, and low environmental impact. Heat-transfer fluids which are liquid over a wide temperature range coupled with low toxicity, low flammability, and low environmental impact are ideal for thermal shock testing.

Materials currently used as heat-transfer fluids for liquid/liquid thermal shock test baths include liquid nitrogen, PFCs, and PFPEs. Each of these heat-transfer fluids has some disadvantage. Liquid nitrogen systems offer limited temperature selectivity at the low temperature end. PFCs and PFPEs may be environmentally persistent.

Constant temperature baths are typically operated over a broad temperature range. Therefore, desirable heat-transfer fluids preferably have a wide liquid range and good low-temperature heat transfer characteristics. A heat-transfer fluid having such properties allows a very wide operating range for the constant temperature bath. Typically, most testing fluids require fluid change-out for wide temperature extremes. Also, good temperature control is essential for accurately predicting physical properties of the heat-transfer fluids.

Heat-transfer fluids which are presently used in this application include: PFCs, perfluoropolyethers (PFPEs), water/glycol mixtures, deionized water, silicone oils, hydrocarbon oils, and hydrocarbon alcohols. Each of these heat-transfer fluids has some disadvantage. PFCs and PFPEs may be environmentally persistent. Water/glycol mixtures are temperature limited, that is, a typical low temperature limit of such mixtures is −40° C. At low temperatures water/glycol mixtures also exhibit relatively high viscosity. Deionized water has a low temperature limit of 0° C. Silicone oils, hydrocarbon oils and hydrocarbon alcohols are typically flammable.

For heat-transfer processing requiring an inert fluid, fluorinated materials are often used. Fluorinated materials typically have low toxicity, are essentially non-irritating to the skin, are non-chemically reactive, are non-flammable, and have high dielectric strength. Fluorinated materials such as perfluorocarbons, perfluoropolyethers, and hydrofluoroethers provide the additional advantage of not depleting the ozone layer in the stratosphere.

As discussed above, perfluorocarbons, perfluoropolyethers, and some hydrofluoroethers have been used for heat-transfer.

Perfluorocarbons (PFCs) exhibit several traits advantageous to the applications discussed above. PFCs have high dielectric strength and high volume resistivity. PFCs are non-flammable and are generally mechanically compatible with materials of construction, exhibiting limited solvency. Additionally, PFCs generally exhibit low toxicity and good operator friendliness. PFCs are manufactured in such a way as to yield a product that has a narrow molecular weight distribution. They do exhibit one important disadvantage, however, and that is long environmental persistence.

Perfluoropolyethers (PFPEs) exhibit many of the same advantageous attributes described for PFCs. They also have the same major disadvantage, i.e., long environmental persistence. In addition, the methods developed for manufacturing these materials yield products that are not of consistent molecular weight and thus are subject to performance variability.

Hydrofluoropolyethers (HFPEs), a class of hydrofluoroethers (HFEs), exhibit some of the same advantageous attributes of PFCs, but differ greatly in two areas. To their credit, they exhibit markedly lower environmental persistence, yielding atmospheric lifetimes on the order of decades rather than millennia. However, some of the HFPEs taught as heat-transfer fluids are a mixture of components of widely disparate molecular weight. Thus, their physical properties may change over time which makes it difficult to predict performance.

Some hydrofluoroethers have been disclosed as heat-transfer fluids. However, the need exists for a heat-transfer fluid which is inert, has high dielectric strength, low electrical conductivity, chemical inertness, thermal stability and effective heat transfer, is liquid over a wide temperature range, has good heat-transfer properties over a wide range of temperatures and also has a shorter atmospheric lifetime, and therefore a lower global warming potential, than existing heat-transfer fluids.

SUMMARY

In one aspect, the present invention comprises a compound which is inert, has high dielectric strength, low electrical conductivity, chemical inertness, thermal stability and effective heat transfer. Additionally, in another embodiment, the present invention comprises a compound that is liquid over a wide temperature range, and has good heat-transfer properties over a wide range of temperature. The compound has the general structure:

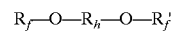

wherein:

O is oxygen;

$R_f$ and $R_f'$ are, independently, a perfluoroaliphatic group, and if $R_f$ and $R_f'$ contain branched alkylene groups, then the number of carbons is at least 4;

$R_h$ is independently a linear, branched or cyclic alkylene group having from 2 to about 8 carbon atoms and at least 4 hydrogen atoms, and wherein the hydrofluoroether compound is free of formal linkage (—O—$CH_2$—O—).

In another aspect, the present invention additionally comprises an apparatus requiring heat-transfer comprising a device, and a mechanism for transferring heat to or from the device comprising a heat-transfer fluid, wherein the heat transfer fluid is represented by the following structure:

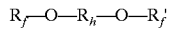

wherein:

O is oxygen;

$R_f$ and $R_f'$ are, independently, a perfluoroaliphatic group; and $R_h$ is independently a linear, branched or cyclic alkylene group having from 2 to about 8 carbon atoms and at least 4 hydrogen atoms, and wherein the hydrofluoroether compound is free of —O—$CH_2$—O—.

Another embodiment of the present invention is a method for transferring heat comprising the steps of: providing a device, providing a mechanism for transferring heat comprising a heat-transfer fluid, and using the heat-transfer fluid to transfer heat to or from the device, wherein the heat-transfer fluid is represented by the following structure:

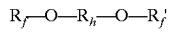

wherein:

O is oxygen;

$R_f$ and $R_f'$ are, independently, a perfluoroaliphatic group; and $R_h$ is independently a linear, branched or cyclic alkylene group having from 2 to about 8 carbon atoms and at least 4 hydrogen atoms, and wherein the hydrofluoroether compound is free of —O—$CH_2$—O—.

DETAILED DESCRIPTION

The present invention provides a hydrofluoroether compound, as well as an apparatus and a method for heat-transfer using the hydrofluoroether compound as a heat-transfer fluid. The apparatus of the present invention comprises a device and a mechanism for transferring heat comprising a heat-transfer fluid.

Perfluorinated means, for the purpose of the present application, that all the hydrogens in a compound have been replaced with fluorine.

Inert means, for the purpose of the present application, generally not chemically reactive under normal conditions of use.

Formal linkage means —O—$CH_2$—O—.

Hydrofluoroether Compound

The present application describes a hydrofluoroether compound and the use of the hydrofluoroether compound as a heat-transfer fluid. The hydrofluoroether compound may be used to heat, cool, and/or maintain the temperature of the device at a select temperature. The hydrofluoroether compound is inert, non-flammable, and environmentally acceptable. Additionally, the hydrofluoroether compound of the present invention exhibits low viscosity throughout the liquid range, and has good heat transfer properties over a wide temperature range.

The hydrofluoroether compound of the present invention is represented by the following structure:

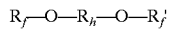

wherein:

O is oxygen;

$R_f$ and $R_f'$ are, independently, a perfluoroaliphatic group. $R_f$ and $R_f'$ are stable, inert, non-polar, preferably saturated, monovalent moieties which are both oleophobic and hydrophobic. $R_f$ and $R_f'$ generally contain at least about 2 carbon atoms, for example about 3 to about 20 carbon atoms, and in specific embodiments from about 3 to about 7 carbon atoms. $R_f$ and $R_f'$ can contain straight chain, branched chain, or cyclic fluorinated alkylene groups or combinations thereof with straight chain, branched chain, or cyclic alkylene groups. Generally, if $R_f$ and $R_f'$ contain branched alkylene groups, then the number of carbons is at least 4. $R_f$ and $R_f'$ are generally free of polymerizable olefinic unsaturation and can optionally contain catenated heteroatoms such as divalent oxygen, or trivalent nitrogen. The $R_f$ and $R_f'$ groups may contain at least 5 fluorine atoms, for example at least 7 fluorine atoms, and in some embodiments at least 9 fluorine atoms (e.g., $CF_3CF_2$—, $CF_3CF_2CF_2CF_2$—, $(CF_3)_2CFCF_2$—, $CF_3CF_2CF_2$—, or the like). Perfluorinated aliphatic groups (i.e., those of the formula $C_xF_{2x+1}$, where x is about 2 to about 8, for example 3 or 4) are examples of embodiments of $R_f$ and $R_f'$.

$R_h$ is independently a linear, branched or cyclic alkylene group having from 2 to about 8 carbon atoms and at least 4 hydrogen atoms, wherein $R_h$ can contain one or more catenated heteroatoms. Examples of $R_h$ include alkylenes, fluoroalkylenes, and the like.

Wherein the hydrofluoroether compound is free of —O—$CH_2$—O—.

The hydrofluoroether compounds of the present invention are generally inert. Additionally, the compounds of the present invention may have high dielectric strength and low electrical conductivity. The compounds additionally are generally thermally stable.

The hydrofluoroether compounds of the present invention are useful as heat transfer liquids. The compounds generally exhibit a liquid phase over a wide temperature range. For example, the compounds are generally liquid to at least about $-50°$ C. Generally, the viscosity of the compounds in the liquid phase is less than 100 centistokes at $-5°$ C. ($100 \times 10^{-6}$ m$^2$/s), preferably less than 50 centistokes ($50 \times 10^{-6}$ m$^2$/s).

The hydrofluoroether compounds of the present invention additionally have low global warming potential values (GWP), in some embodiments under 500. GWP is determined using a calculated value for atmospheric lifetime and an experimentally determined infrared absorbance data integrated over the spectral region of interest, typically 500 to 2500 cm$^{-1}$. A detailed description of GWP can be found, for example in U.S. Pat. No. 5,925,611, which is incorporated by reference.

The hydrofluoroether compounds of the present invention are generally prepared by alkylation of perfluorinated acyl fluorides with polyfunctional alkylating agents, for example dimesylates and ditosylates using fluoride ion in a polar aprotic solvent.

Apparatus

In certain embodiments, the invention includes an apparatus requiring heat transfer. The apparatus comprises a device and a mechanism for transferring heat to or from the device using a heat-transfer fluid. Such apparatus include refrigeration systems, cooling systems, testing equipment, and machining equipment.

Examples of an apparatus of the present invention include, but are not limited to, test heads used in automated test equipment for testing the performance of semiconductor dice; wafer chucks used to hold silicon wafers in ashers, steppers, etchers, PECVD tools; constant temperature baths, and thermal shock test baths.

Device

In certain embodiments, the present invention comprises a device. The device is defined herein as a component, work-piece, assembly, etc. to be cooled, heated or maintained at a selected temperature. Such devices include electrical components, mechanical components and optical components. Examples of devices of the present invention include, but are not limited to microprocessors, wafers used to manufacture semiconductor devices, power control semiconductors, electrical distribution switch gear, power transformers, circuit boards, multi-chip modules, packaged and unpackaged semiconductor devices, chemical reactors, nuclear reactors, fuel cells, lasers, and missile components.

Heat Transfer Mechanism

In certain embodiments, the present invention comprises a mechanism for transferring heat. Heat is transferred by placing the heat transfer mechanism in thermal contact with the device. The heat transfer mechanism, when placed in thermal contact with the device, removes heat from the device or provides heat to the device, or maintains the device at a selected temperature. The direction of heat flow (from device or to device) is determined by the relative temperature difference between the device and the heat transfer mechanism.

The heat transfer mechanism comprises the heat-transfer fluid of the present invention.

Additionally, the heat transfer mechanism may include facilities for managing the heat-transfer fluid, including, but not limited to: pumps, valves, fluid containment systems, pressure control systems, condensers, heat exchangers, heat sources, heat sinks, refrigeration systems, active temperature control systems, and passive temperature control systems.

Examples of suitable heat transfer mechanisms include, but are not limited to, temperature controlled wafer chucks in PECVD tools, temperature controlled test heads for die performance testing, temperature controlled work zones within semiconductor process equipment, thermal shock test bath liquid reservoirs, and constant temperature baths.

In some systems, such as etchers, ashers, PECVD chambers, thermal shock testers, the upper desired operating temperature may be as high as 150° C.

Method

The present invention additionally comprises a method for transferring heat comprising the steps of: providing a device, providing a mechanism for transferring heat comprising a heat-transfer fluid, and using the heat-transfer fluid to transfer heat to or from the device, wherein the heat-transfer fluid is represented by the following structure:

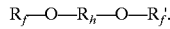

EXAMPLES

The present invention will be further described with reference to the following nonlimiting examples and test methods. All parts, percentages, and ratios are by weight unless otherwise specified.

Example 1

1,1,1,2,2,3,3-Heptafluoro-3-(3-heptafluoropropyloxy-propoxy)-propane

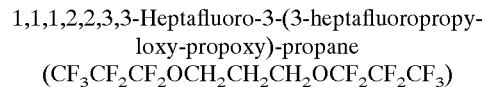

Into a clean dry 600 mL Parr reactor equipped with stirrer, heater and thermocouple were added 20.1 g (0.35 mole) of anhydrous potassium fluoride, 49.8 g (0.13 mole) of 1,3-propanediol di-p-tosylate (TCI America), 4.4 grams of Adogen™ 464 (Aldrich) and 300 ml. of anhydrous diglyme (anhydrous diethylene glycol dimethyl ether, available from Sigma Aldrich Chemical Co. used in all subsequent syntheses). The anhydrous potassium fluoride used in this synthesis, and in all subsequent syntheses, was spray dried, stored at 125° C. and ground shortly before use. The reactor was sealed and cooled to about −50° C. and a vacuum pump used to evacuate the vapor space. 53.5 g (0.30 mole) of $C_2F_5C(O)F$ (approximately 95.0 percent purity) was added to the sealed reactor. The reactor and its contents were then heated to 75° C. and held for 21 hours. Pressure decreased from 86 psig to 12.1 psig during the reaction. The reactor contents were allowed to cool and excess pressure was vented. The reactor contents were added to a 500 ml. round bottom flask equipped with a mechanical stirrer, temperature probe, water condenser and Dean-Stark receiver. Deionized water (200 ml) was added to the flask and the mixture steam distilled to give 49.0 grams of lower phase distillate containing 65.8% of $C_3F_7OC_3H_6OC_3F_7$ as determined by gas-chromatography. The crude product was azeotropically distilled from 100 g of 22.5% aqueous potassium hydroxide. The product was water washed, dried with anhydrous sodium sulfate and fractionally distilled to provide 8.2 g of 97.3% purity 1,1,1,2,2,3,3-heptafluoro-3-(3-heptafluoropropyloxy-propoxy)-propane. The boiling point was 159° C. and the structure was confirmed by gas chromatography-mass spectrometry (gc-ms). The viscosity was 9 centistokes ($9 \times 10^{-6}$ m$^2$/s) at −50° C. measured using a Cannon-Fenske viscometer and a Wescan Model 221 viscosity timer.

Example 2

1,1,1,2,2,3,3,4,4-Nonafluoro-4-(3-nonafluorobutyloxy-propoxy)-butane (CF$_3$CF$_2$CF$_2$CF$_2$OCH$_2$CH$_2$CH$_2$OCF$_2$CF$_2$CF$_2$CF$_3$)

This compound was prepared by the method of Example 1 using 24.0 g (0.41 mole) potassium fluoride, 75.0 g 1,3-propanediol di-p-tosylate (Alfa-Aesar), 4.7 g. Adogen™ 464 and 200 ml of diglyme, and 75.0 g CF$_3$CF$_2$CF$_2$C(O)F (approximately 95% purity). The reactor contents were heated to 75° C. and held 120 hours. The final pressure was 8.0 psig. The reactor was vented and the contents added to 1-liter round bottom flask. 200 grams of 22.5% KOH was added to the flask and the contents steam distilled and then water washed to provide 52.8 g of material containing 64.5% of CF$_3$CF$_2$CF$_2$CF$_2$OC$_3$H$_6$OCF$_2$CF$_2$CF$_2$CF$_3$ as determined by gas chromatography. The crude product was fractionally distilled to provide 19.3 g of 100% pure 1,1,1,2,2,3,3,4,4-nonafluoro-4-(3-nonafluorobutyloxy-propoxy)-butane. The boiling point was 190° C. and the structure was confirmed by gc-ms. The viscosity was 25 centistokes ($25 \times 10^{-6}$ m$^2$/s) at −50° C. measured using a Cannon-Fenske viscometer and a Wescan Model 221 viscosity timer.

Example 3

1,1,1,2,2,3,3-Heptafluoro-3-(2-heptafluoropropyloxy-ethoxy)-propane ($CF_3CF_2CF_2OCH_2CH_2OCF_2CF_2CF_3$)

This compound was prepared by the method of Example 1 using 19.4 g (0.33 mole) potassium fluoride, 48.9 g (0.13 mole) of 1,2-ethylene glycol di-p-tosylate (Aldrich), 4.7 g of Adogen™ 464 and 302.7 g of diglyme and 47.0 grams of $CF_3CF_2CF_2C(O)F$ (approximately 95% purity). The reactor was held at 50° C. for 40 hours. The reactor was vented and the contents were added to a 3-liter round bottom flask equipped with a mechanical stirrer, temperature probe, water condenser and Dean-Stark receiver. The contents of another reaction run similarly were also added to the 3-Liter flask. 150 grams of 22.5% KOH was added to the flask and the mixture steam distilled and then water washed to give 41.1 grams of material containing 90.2% of $CF_3CF_2CF_2OC_2H_4OCF_2CF_2CF_3$ as determined by gas chromatography. The crude product was fractionally distilled to provide 21.6 grams of 99.4% purity of 1,1,1,2,2,3,3-heptafluoro-3-(2-heptafluoropropyloxy-ethoxy)-propane. The boiling point was 145° C. and the structure was confirmed by gc-ms. The viscosity was 7 centistokes ($7 \times 10^{-6}$ m$^2$/s) at −50° C. measured using a Cannon-Fenske viscometer and a Wescan Model 221 viscosity timer.

Example 4

1,1,1,2,2,3,3,4,4,5,5-Undecafluoro-5-(3-undecafluoropentyloxy-propoxy)-pentane ($CF_3CF_2CF_2CF_2CF_2OCH_2CH_2CH_2OCF_2CF_2CF_2CF_2CF_3$)

This compound was prepared by the method of Example 1 using 19.3 g (0.33 mole) potassium fluoride, 50.5 g (0.13 mole) of 1,3-propanediol di-p-tosylate (Alfa Aesar), 3.8 g of Adogen™ 464 and 251.4 g of diglyme and 69 grams of $CF_3CF_2CF_2CF_2C(O)F$ (approximately 95% purity). The reactor was held at 90° C. for 24 hours. Final reactor pressure was 1.5 psig. The reactor contents were added to a 2-liter round bottom flask equipped with a mechanical stirrer, temperature probe, water condenser and Dean-Stark receiver. 120 grams of 22.5% KOH was added to the flask and the mixture steam distilled and then water washed to give 46.9 grams of material containing 74.1% of $CF_3CF_2CF_2CF_2CF_2OC_3H_6OCF_2CF_2CF_2CF_2CF_3$ as determined by gas chromatography. The crude product was fractionally distilled to provide 23.2 grams of 98.2% pure 1,1,1,2,2,3,3,4,4,5,5-undecafluoro-5-(3-undecafluoropentyloxy-propoxy)-pentane. The boiling point was 208.1° C. and the structure was confirmed by gc-ms. The viscosity was 85 centistokes ($85 \times 10^{-6}$ m$^2$/s) at −50° C. measured using a Cannon-Fenske viscometer and a Wescan Model 221 viscosity timer.

Example 5

1,1,1,2,2,3,4,5,5,5-Decafluoro-3-{3-[1,2,2,3,3,3-hexafluoro-1-(1,2,2,2-tetrafluoro-1-trifluoromethyl-ethyl)-propoxy]-propoxy}-4-trifluoromethyl-pentane ($CF_3CF_2CF[CF(CF_3)_2]OCH_2CH_2CH_2OCF[CF(CF_3)_2]CF_2CF_3$)

This compound was prepared by the method of Example 1 using 8.4 g (0.14 mole) potassium fluoride, 25.0 g (0.06 mole) of 1,3-propanediol di-p-tosylate (Alfa Aesar), 1.5 g of Adogen™ 464 and 150 ml of diglyme and 34.3 grams of $CF_3CF_2C(O)CF(CF_3)_2$ (approximately 99% purity). Reactor was held at 100° C. for 22 hours. Final reactor pressure was 8.1 psig. The reactor contents were added to a round bottom flask equipped with a mechanical stirrer, temperature probe, water condenser and Dean-Stark receiver. 40 grams of 37.5% KOH was added to the flask and the mixture steam distilled and then water washed to give 19.3 grams of material containing 47.3% of $CF_3CF_2CF[CF(CF_3)_2]OCH_2CH_2CH_2OCF[CF(CF_3)_2]CF_2CF_3$ as determined by gas chromatography. The structure was confirmed by gc-ms.

Example 6

1,1,1,2,2,3,3,4,4-Nonafluoro-4-(4-nonafluorobutyloxy-butoxy)butane ($CF_3CF_2CF_2CF_2OCH_2CH_2CH_2CH_2OCF_2CF_2CF_2CF_3$)

In a manner similar to that described in Example 1, potassium fluoride (20.7 g, 0.356 mole), 1,4-butanediol dimethanesulfonate (40 g, 0.162 mole, Aldrich), Adogen™ 464 (8.8 g of a 55% solution in anhydrous diglyme) and anhydrous diglyme (300 ml) were combined in a 600 mL Parr reactor. After the reactor had been cooled and evacuated as described above, n-$C_3F_7COF$ (84.2 g of 95% purity, 0.37 mole) was added and the reactor then heated to 75° C. for 19 hours. The temperature was then raised to 80° C. for an additional 20 hours. Pressure decreased from 72 psig to 25 psig during the reaction. The reactor contents were allowed to cool and excess pressure was vented. The reactor contents were transferred to a 1 L round bottom flask with about 300 mL of water. The mixture was azeotropically distilled as described in Example 1 to obtain 48 g of a lower fluorochemical phase after phase separation and washing which contained 66% of the desired $C_4F_9OC_4H_8OC_4F_9$ product. The crude product was azeotropically distilled from about 100 g of 45% potassium hydroxide using the same apparatus as for the first distillation and the lower fluorochemical phase water washed and fractionally distilled to provide 18.3 g of 99.5% purity 1,1,1,2,2,3,3,4,4-nonafluoro-4-(4-nonafluorobutyloxy-butoxy)butane. The boiling point was 208° C. and the structure was confirmed by gc-ms. The viscosity was 41 centistokes ($41 \times 10^{-6}$ m$^2$/s) at −50° C. measured using a Cannon-Fenske viscometer and a Wescan Model 221 viscosity timer.

Example 7 n,i-$C_4F_9OC_3H_6On$,i-$C_4F_9$ (This product is an inseparable mixture of n-$C_4F_9$ and iso-$C_4F_9$ groups on either end of the molecule)

In a manner similar to that described in Example 1, potassium fluoride (17.4 g, 0.3 mole), 1,3-propanediol di-p-tosylate (55 g, 0.143 mole, Aldrich), Adogen™ 464 (8.3 g of a 55% solution in anhydrous diglyme) and anhydrous diglyme (271 g) were combined in a 600 mL Parr reactor. After the reactor had been cooled and evacuated as described above, a mixture of n-$C_3F_7COF$ and i-$C_3F_7COF$ (100 g of 70% purity, 0.324 mole, about 60% iso and 40% normal) was added and the reactor then heated to 75° C. for about 64 hours. Pressure decreased from 115 psig to 65 psig during the reaction. The reactor contents were allowed to cool and excess pressure was vented. The reactor contents were transferred to a 1 L round bottom flask with about 300 mL of water. The mixture was azeotropically distilled as described in Example 1 to obtain 58.4 g of a lower fluorochemical phase after phase separation and washing which contained 85% of the desired $C_4F_9OC_3H_6OC_4F_9$ product. The crude product was again azeotropically distilled from about 100 g of 45% potassium hydroxide. The lower fluorochemical phase was water washed and fractionally distilled to provide 32.2 g of 95.5% purity product. The boiling range was 188–190° C. and the structure was confirmed by gc-ms. The viscosity was 35 centistokes ($35 \times 10^{-6}$ m$^2$/s) at −50° C. measured using a Cannon-Fenske viscometer and a Wescan Model 221 viscosity timer.

Example 8 n,i-$C_4F_9OC_4H_8On$,i-$C_4F_9$ (This product is an inseparable mixture of n-$C_4F_9$ and iso-$C_4F_9$ groups on either end of the molecule)

In a manner similar to that described in Example 1, potassium fluoride (17.1 g, 0.29 mole), 1,4-butanediol dimethanesulfonate (30.1 g, 0.12 mole, Aldrich), Adogen™ 464 (4.5 g of a 55% solution in anhydrous diglyme) and anhydrous diglyme (278 g) were combined in a 600 mL Parr reactor. After the reactor had been cooled and evacuated as described above, a mixture of n-$C_3F_7$COF and i-$C_3F_7$COF (73.6 g of 70% purity, 0.24 mole, about 60% iso and 40% normal) was added and the reactor then heated to 75° C. for about 64 hours. Pressure decreased from 100 psig to 50 psig during the reaction. The reactor contents were allowed to cool and excess pressure was vented. The reactor contents were transferred to a 1 L round bottom flask with about 300 mL of water. The mixture was azeotropically distilled as described in Example 1 to obtain 28 g of a lower fluorochemical phase after phase separation and washing which contained 60% of the desired $C_4F_9OC_4H_8OC_4F_9$ product. The crude product was again azeotropically distilled from about 100 g of 45% potassium hydroxide. After separation and water washing of the lower phase, this sample was combined with another sample prepared in essentially the same manner and the combined sample was fractionally distilled to provide 19.2 g of 90.7% purity product. The boiling range was 206–208° C. and the structure was confirmed by gc-ms. The viscosity was 51 centistokes ($51 \times 10^{-6}$ m$^2$/s) at −50° C. measured using a Cannon-Fenske viscometer and a Wescan Model 221 viscosity timer.

Example 9

1,1,1,2,2,3,3,4,4-Nonafluoro-4-(2-nonafluorobutyloxy-ethoxy)butane
($CF_3CF_2CF_2CF_2OCH_2CH_2OCF_2CF_2CF_2CF_3$)

In a manner similar to that described in Example 1, potassium fluoride (18.8 g, 0.32 mole), 1,2-ethanediol di-p-tosylate (50 g, 0.135 mole, Aldrich), Adogen™ 464 (5.5 g of a 55% solution in anhydrous diglyme) and anhydrous diglyme (278 g) were combined in a 600 mL Parr reactor. After the reactor had been cooled and evacuated as described above, n-$C_3F_7$COF (61.4 g of 95% purity, 0.27 mole) was added and the reactor then heated to 75° C. for about 30 hours. Pressure decreased from 65 psig to −11.9 psig during the reaction. Since the reactor was initially evacuated, the final pressure assuming complete reaction and no unreactive volatile materials remaining would be negative as measured by the pressure transducer. The reactor contents were allowed to cool to ambient temperature and the reactor opened. The reactor contents were transferred to a 1 L round bottom flask with about 300 mL of water. The mixture was azeotropically distilled as described in Example 1 to obtain 29 g of a lower fluorochemical phase after phase separation and washing which contained 42% of the desired $C_4F_9OC_2H_4OC_4F_9$ product. In this case, the product was first distilled using a concentric tube column and a distillation cut from 175–182° C. was subsequently treated with 45% potassium hydroxide in the usual manner. The purity at this stage was now 95.9% of the desired diether as confirmed by gc-ms.

Example 10

1,1,1,2,2,3,3,4,4-Nonafluoro-4-(2-(2-nonafluorobutyloxy-ethoxy-ethoxy)butane
($CF_3CF_2CF_2CF_2OCH_2CH_2OCH_2CH_2OCF_2CF_2CF_2CF_3$)

In a manner similar to that described in Example 1, potassium fluoride (16.8 g, 0.29 mole) diethylene glycol di-p-tosylate (50 g, 0.121 mole, Aldrich), Adogen™ 464 (6.2 g of a 55% solution in anhydrous diglyme) and anhydrous diglyme (278 g) were combined in a 600 mL Parr reactor. After the reactor had been cooled and evacuated as described above, n-$C_3F_7$COF (53.5 g of 95% purity, 0.24 mole) was added and the reactor then heated to 75° C. for about 17 hours. Pressure decreased from 47 psig to −1.6 psig during the reaction. The reactor contents were allowed to cool to ambient temperature and the reactor opened. The reactor contents were transferred to a 1 L round bottom flask with about 300 mL of water. The mixture was azeotropically distilled as described in Example 1 to obtain 46 g of a lower fluorochemical phase after phase separation and washing which contained 75% of the desired $C_4F_9OC_2H_4OC_2H_4OC_4F_9$ product. This material was not subsequently treated with KOH and was found to be 90% desired product having a distillation range of 218–219° C. The viscosity was 64 centistokes ($64 \times 10^{-6}$ m$^2$/s) at −50° C. measured using a Cannon-Fenske viscometer and a Wescan Model 221 viscosity timer.

Example 11

1,1,2,2,3,3-Hexafluoro-1-[3-(1,1,2,2,3,3-hexafluoro-3-trifluoromethoxy-propoxy)-propoxy] -3-trifluoromethoxy-propane
($CF_3OCF_2CF_2CF_2OCH_2CH_2CH_2OCF_2CF_2CF_2OCF_3$)

This compound was prepared by the method of Example 1 using 23.9 g (0.41 mole) potassium fluoride, 49.5 g (0.13 mole) 1,3-propanediol di-p-tosylate (Alfa-Aesar), 4.1 g Adogen™ 464 and 300 ml of diglyme, and 72.4 g $CF_3OCF_2CF_2C(O)F$ (approximately 95% purity). The reactor contents were heated to 75° C. and held 89 hours. The reactor was vented and the contents added to 1-liter round bottom flask. 150 grams of water were added to the flask and the contents steam distilled and then water washed to provide 58.3 g of material containing 93.6% of $CF_3OCF_2CF_2CF_2OC_3H_6OCF_2CF_2CF_2OCF_3$ as determined by gas chromatography. The crude product was fractionally distilled to provide 18.6 g of 97.3% pure 1,1,2,2,3,3-Hexafluoro-1-[3-(1,1,2,2,3,3-hexafluoro-3-trifluoromethoxy-propoxy)-propoxy] -3-trifluoromethoxy-propane. The boiling point was 191° C. and the structure was confirmed by gc-ms. The viscosity was 19 centistokes ($19 \times 10^{-6}$ m$^2$/s) at −50° C. measured using a Cannon-Fenske viscometer and a Wescan Model 221 viscosity timer.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims as set forth herein as follows.

What is claimed is:

1. A compound represented by the general formula:

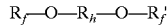

wherein:
O is oxygen;
$R_f$ and $R_f'$ are, independently, a perfluoroaliphatic group, and if $R_f$ and $R_f'$ contain branched alkylene groups, then $R_f$ and $R_f'$ contain at least 4 carbons;
$R_h$ is independently a linear, branched or cyclic alkylene group having from 2 to about 8 carbon atoms and at least 4 hydrogen atoms, and
wherein the hydrofluoroether compound is free of —O—CH$_2$—O—.

2. The compound of claim 1 wherein $R_f$ and $R_f'$ contain, independently, at least about 2 carbon atoms.

3. The compound of claim 2 wherein $R_f$ and $R_f'$ contain, independently, about 3 to about 20 carbon atoms.

4. The compound of claim 2 wherein $R_f$ and $R_f'$ contain, independently, 3 to about 7 carbon atoms.

5. The compound of claim 1 wherein $R_f$ and $R_f'$ contain at least 5 fluorine atoms.

6. The compound of claim 5 wherein $R_f$ and $R_f'$ contain, independently, at least 7 fluorine atoms.

7. The compound of claim 5 wherein $R_f$ and $R_f'$ contain, independently, at least 9 fluorine atoms.

8. The compound of claim 1 wherein $R_f$ and $R_f'$ are, independently, $C_xF_{2x+1}$, where x is about 2 to about 8.

9. The compound of claim 8 wherein x is 3 or 4.

10. The compound of claim 1 wherein the compound has a viscosity is less than 100 centistokes ($100 \times 10^{-6}$ m$^2$/s) at $-50°$ C.

11. The compound of claim 10 wherein the compound has a viscosity of less than 50 centistokes ($50 \times 10^{-6}$ m$^2$/s) at $-50°$ C.

12. An apparatus requiring heat transfer comprising:
(a) a device; and
(b) a mechanism for transferring heat to or from the device, comprising using a heat-transfer fluid,
wherein the heat transfer fluid is represented by the following structure:

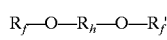

wherein:
O is oxygen;
$R_f$ and $R_f'$ are, independently, a perfluoroaliphatic group; and
$R_h$ is independently a linear, branched or cyclic alkylene group having from 2 to about 8 carbon atoms and at least 4 hydrogen atoms, and
wherein the hydrofluoroether compound is free of —O—CH$_2$—O—.

13. The apparatus according to claim 12, wherein the device is selected from the group consisting of microprocessors, wafers used to manufacture semiconductor devices, power control semiconductors, electrical distribution switch gear, power transformers, circuit boards, multi-chip modules, packaged and unpackaged semiconductor devices, chemical reactors, nuclear reactors, fuel cells, lasers, and missile components.

14. The apparatus according to claim 12, wherein the device is heated.

15. The apparatus according to claim 12, wherein the device is cooled.

16. The apparatus according to claim 12, wherein the device is maintained at a selected temperature.

17. The apparatus according to claim 12, wherein the mechanism for transferring heat is selected from the group consisting of temperature controlled wafer chucks in PECVD tools, temperature controlled test heads for die performance testing, temperature controlled work zones within semiconductor process equipment, thermal shock test bath liquid reservoirs, and constant temperature baths.

18. A method for transferring heat comprising the steps of:
(a) providing a device; and
(b) using a heat-transfer fluid to transfer heat to or from the device,
wherein the heat-transfer fluid is represented by the following structure:

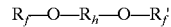

wherein:
O is oxygen;
$R_f$ and $R_f'$ are, independently, a perfluoroaliphatic group; and
$R_h$ is independently a linear, branched or cyclic alkylene group having from 2 to about 8 carbon atoms and at least 4 hydrogen atoms, and
wherein the hydrofluoroether compound is free of —O—CH$_2$—O—.

* * * * *

UNITED STATES PATENT AND TRADEMARK OFFICE
CERTIFICATE OF CORRECTION

PATENT NO. : 6,953,082 B2
DATED : October 11, 2005
INVENTOR(S) : Costello, Michael G.

It is certified that error appears in the above-identified patent and that said Letters Patent is hereby corrected as shown below:

Title page,
Item [56], References Cited, U.S. PATENT DOCUMENTS, delete "Touslgnant et al." and insert -- Tousignant et al. --.

Column 6,
Line 41, delete "-5°C." and insert -- 50°C. --.

Column 9,
Line 20, delete "$CF_3CF_2CF_2OC_2H_4OCF_2CF_2CF_3$" and insert -- $CF_3CF_2CF_2OC_2H_4OCF_2CF_2CF_3$ --.

Column 10,
Line 50, delete "n-C $_4F_9$" and insert -- $n-C_4F_9$ --.

Column 12,
Line 23, delete "n-C $_3F_7COF$" and insert -- $n-C_3F_7COF$ --.

Signed and Sealed this

Twenty-eighth Day of March, 2006

JON W. DUDAS
*Director of the United States Patent and Trademark Office*